United States Patent
Turovskiy (10) Patent No.: US 11,950,826 B2
(45) Date of Patent: Apr. 9, 2024

(54) CATHETER ASSEMBLIES COMPRISING A DIRECT HEATING ELEMENT FOR RENAL NEUROMODULATION AND ASSOCIATED SYSTEMS AND METHODS

(71) Applicant: Medtronic Ireland Manufacturing Unlimited Company, Dublin (IE)

(72) Inventor: Roman Turovskiy, San Francisco, CA (US)

(73) Assignee: Medtronic Ireland Manufacturing Unlimited Company, Dublin (IE)

(*) Notice: Subject to any disclaimer, the term of this patent is extended or adjusted under 35 U.S.C. 154(b) by 600 days.

(21) Appl. No.: 16/910,668

(22) Filed: Jun. 24, 2020

(65) Prior Publication Data

US 2020/0315683 A1 Oct. 8, 2020

Related U.S. Application Data

(62) Division of application No. 14/271,730, filed on May 7, 2014, now Pat. No. 10,709,490.

(51) Int. Cl.
*A61B 18/14* (2006.01)
*A61B 18/08* (2006.01)
*A61B 18/00* (2006.01)

(52) U.S. Cl.
CPC ........ *A61B 18/082* (2013.01); *A61B 18/1492* (2013.01); *A61B 2018/0022* (2013.01); *A61B 2018/00285* (2013.01); *A61B 2018/00404* (2013.01); *A61B 2018/00434* (2013.01); *A61B 2018/00511* (2013.01); *A61B 2018/00577* (2013.01); *A61B 2018/00714* (2013.01); *A61B 2018/1435* (2013.01); *A61B 2018/1465* (2013.01)

(58) Field of Classification Search
CPC .. A61B 2018/0022; A61B 2018/00285; A61B 18/1492
See application file for complete search history.

(56) References Cited

U.S. PATENT DOCUMENTS

| | | | | |
|---|---|---|---|---|
| 2011/0264086 A1* | 10/2011 | Ingle | ........ | A61B 18/1492 606/33 |
| 2012/0071870 A1* | 3/2012 | Salahieh | ........ | A61B 1/00181 606/33 |
| 2013/0012866 A1* | 1/2013 | Deem | ........ | A61N 1/36114 607/116 |

(Continued)

*Primary Examiner* — Michael F Peffley
*Assistant Examiner* — Samantha M Good
(74) *Attorney, Agent, or Firm* — Shumaker & Sieffert, P.A.

(57) ABSTRACT

Catheter apparatuses, systems, and methods for achieving renal neuromodulation by intravascular access are disclosed herein. One aspect of the present technology, for example, is directed to a treatment device having a direct heating element configured to be delivered to a renal blood vessel. The treatment device is selectively transformable between a delivery or low-profile state and a deployed state. The direct heating element is housed within an occlusion element which is sized and shaped so that the direct heating element contacts an interior wall of the occlusion element, an outer wall of which is simultaneously in contact with the inner wall of a renal blood vessel when the treatment assembly is in the deployed state. The direct heating element is configured to apply thermal energy to heat neural fibers that contribute to renal function.

21 Claims, 6 Drawing Sheets

(56) References Cited

U.S. PATENT DOCUMENTS

2013/0165914 A1\* 6/2013 Satake ............... A61B 18/1492
606/33
2013/0211176 A1\* 8/2013 Habib ..................... A61N 7/00
606/41

\* cited by examiner

CATHETER ASSEMBLIES COMPRISING A DIRECT HEATING ELEMENT FOR RENAL NEUROMODULATION AND ASSOCIATED SYSTEMS AND METHODS

APPLICATIONS INCORPORATED BY REFERENCE

This application is a divisional application of U.S. patent application Ser. No. 14/271,730 titled "Catheter Assemblies Comprising a Direct Heating Element for Renal Neuromodulation and Associated Systems and Methods," filed on May 7, 2014, which issued as U.S. Pat. No. 10,709,490, the entirety of which is hereby incorporated by reference herein.

The following applications are also incorporated herein by reference in their entireties:

U.S. patent application Ser. No. 13/793,647, filed Mar. 11, 2013;

U.S. patent application Ser. No. 13/281,360, filed Oct. 25, 2011;

U.S. patent application Ser. No. 13/281,361, filed Oct. 25, 2011; and

U.S. patent application Ser. No. 13/281,395, filed Oct. 25, 2011.

As such, components and features of embodiments disclosed in these applications may be combined with various components and features disclosed in the present application.

TECHNICAL FIELD

The present technology relates generally to renal neuromodulation and associated systems and methods. In particular, several embodiments are directed to ablation catheter assemblies including a direct heating element for intravascular renal neuromodulation and associated systems and methods.

BACKGROUND

The sympathetic nervous system (SNS) is a primarily involuntary bodily control system typically associated with stress responses. Fibers of the SNS innervate tissue in almost every organ system of the human body and can affect characteristics such as pupil diameter, gut motility, and urinary output. Such regulation can have adaptive utility in maintaining homeostasis or preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine ("NE") spillover rates in patients with essential hypertension.

Cardio-renal sympathetic nerve hyperactivity can be particularly pronounced in patients with heart failure. For example, an exaggerated NE overflow from the heart and kidneys of plasma is often found in these patients. Heightened SNS activation commonly characterizes both chronic and end stage renal disease. In patients with end stage renal disease, NE plasma levels above the median have been demonstrated to be predictive of cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium ($Na^+$) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal blood vessel (e.g., via RF ablation) have been shown to reduce blood pressure in patients with treatment-resistant hypertension.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

DETAILED DESCRIPTION

The present technology is directed to apparatuses, systems, and methods for achieving thermally-induced renal neuromodulation (i.e., rendering neural fibers that innervate the kidney inert, inactive or otherwise completely or partially reduced in function) by percutaneous transluminal intravascular access. In particular, embodiments of the present technology relate to catheters and catheter assemblies having a direct heating element and an occlusion element, such as a balloon, around the direct heating element. The catheter assembly is configurable between a delivery or low-profile state configured to pass through the vasculature and a deployed state in which the direct heating element has a radially expanded shape (e.g., generally helical/spiral or coil). The direct heating element is configured to deliver energy (e.g., thermal energy) to a wall of a renal artery after the direct heating element has been positioned at a target site in the renal artery via a catheter along a percutaneous transluminal path (e.g., a femoral artery puncture, an iliac artery and the aorta, a radial artery, or another suitable intravascular path). The occlusion element is sized and shaped so that in an expanded configuration the direct heating element contacts the interior surface of the occlusion element and the exterior surface of the occlusion element contacts the wall of the renal artery. In the expanded configuration, the occlusion element at least partially or at least substantially occludes blood flow in the renal artery to mitigate heat loss to the blood and thereby enhance the heat transfer from the direct heating element to the wall of the renal artery during operation. This configuration offers a relatively low profile. In addition, in embodiments wherein the occlusion element is an expandable balloon, this configuration presents a suitable platform for pleating and folding.

Specific details of several embodiments of the technology are described below with reference to FIGS. 1-5. Although many of the embodiments are described below with respect to devices, systems, and methods for intravascular modulation of renal nerves using a direct heating element, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-5.

As used herein, the terms "distal" and "proximal" define a position or direction with respect to the treating clinician or clinician's control device (e.g., a handle assembly). "Distal" or "distally" are a position distant from or in a direction away from the clinician or clinician's control device. "Proximal" and "proximally" are a position near or in a direction toward the clinician or clinician's control device.

I. Renal Neuromodulation

Renal neuromodulation is the partial or complete incapacitation or other effective disruption of nerves innervating the kidneys. In particular, renal neuromodulation comprises inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and in particular conditions associated with central sympathetic over stimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, osteoporosis, and sudden death. The reduction of efferent and/or afferent neural signals contributes to the systemic reduction of sympathetic tone/drive, and renal neuromodulation is expected to be useful in treating several conditions associated with systemic sympathetic over activity or hyperactivity. Renal neuromodulation can potentially benefit a variety of organs and bodily structures innervated by sympathetic nerves.

Various techniques can be used to partially or completely incapacitate neural pathways, such as those innervating the kidney. The purposeful application of energy (e.g., electrical energy, thermal energy) to tissue by energy delivery element(s) can induce one or more desired thermal heating effects on localized regions of the renal artery and adjacent regions of the renal plexus, which lay intimately within or adjacent to the adventitia of the renal artery. The purposeful application of the thermal heating effects can achieve neuromodulation along all or a portion of the renal plexus.

The thermal heating effects can include both thermal ablation and non-ablative thermal alteration or damage (e.g., via sustained heating and/or resistive heating). Desired thermal heating effects may include raising the temperature of target neural fibers above a predetermined threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for ablative thermal alteration.

More specifically, exposure to thermal energy (heat) in excess of a body temperature of about 37° C., but below a temperature of about 45° C., may induce thermal alteration via moderate heating of the target neural fibers or of vascular structures that perfuse the target fibers. In cases where vascular structures are affected, the target neural fibers are denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the type of heat exposure utilized to induce the thermal neuromodulation, a reduction in renal sympathetic nerve activity (RSNA) is expected.

II. Selected Embodiments of Neuromodulation Systems

Figure 1:
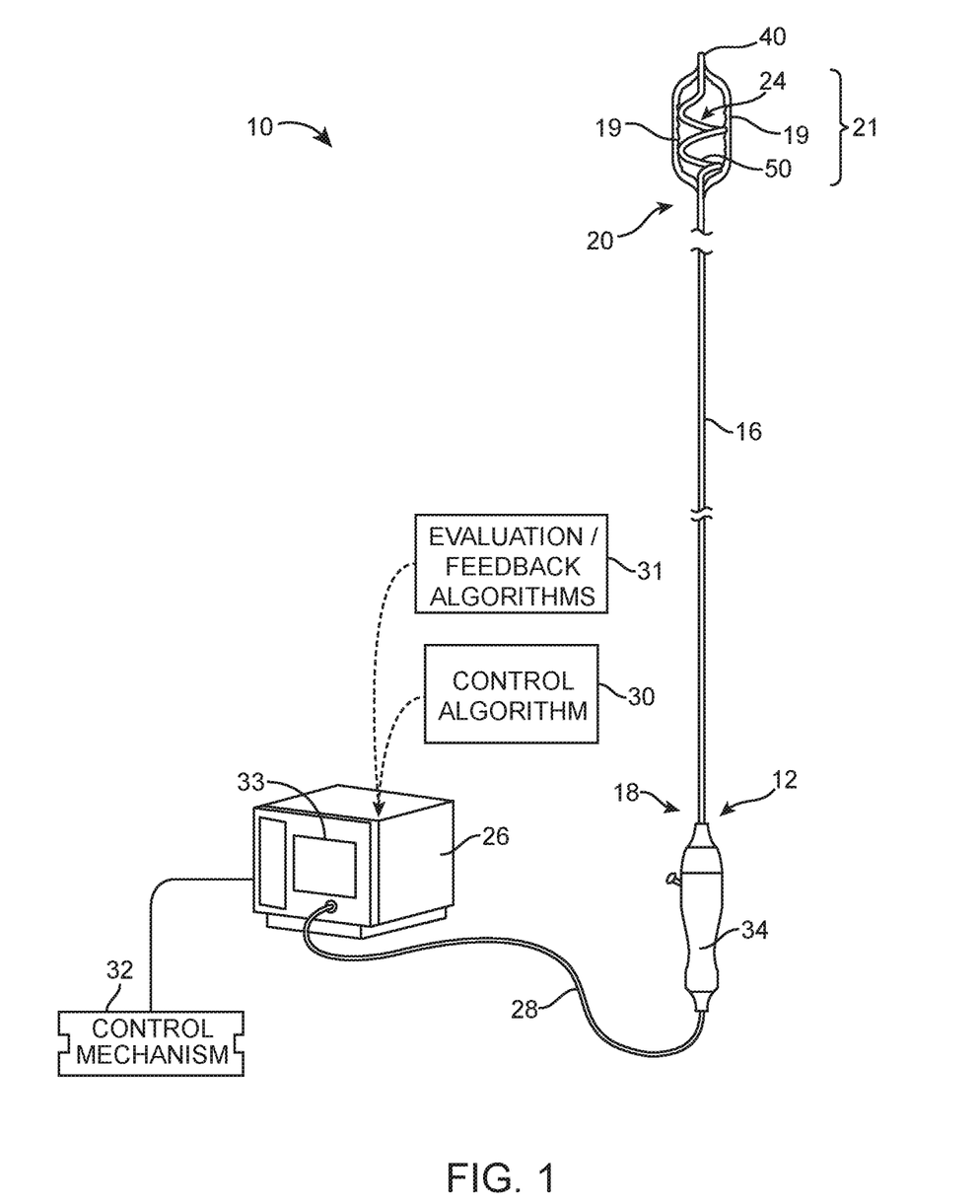
FIG. 1 is a partially schematic diagram of a neuromodulation system configured in accordance with an embodiment of the present technology.

FIG. 1 illustrates a renal neuromodulation system 10 ("system 10") configured in accordance with an embodiment of the present technology. The system 10 includes an intravascular catheter 12 and a thermal energy generator 26 operably coupled to the catheter 12. The catheter 12 can include an elongated shaft 16 having a proximal portion 18 and a distal portion 20, and the catheter 12 can also have a handle 34 at the proximal region of the proximal portion 18. The catheter 12 can further include a therapeutic assembly 21 at the distal portion 20 of the elongated shaft 16. The therapeutic assembly 21, for example, can be a treatment section that is attached to the distal portion 20 or otherwise defines a section of the distal portion 20. As explained in further detail below, the therapeutic assembly 21 can include an occlusion element 19, a control member 50 in the occlusion element 19, and a direct heating element 24 carried by the control member 50.

The direct heating element 24 can be a material configured to increase in temperature in response to energy input from the energy generator 26, thus providing thermal energy to a target tissue by conduction, convection or thermal radiation. The direct heating element 24 can include one or more heating wires secured over the control member 50. The one or more heating wires may be formed of any suitable conductive and/or resistive material, including for example constantan, stainless steel, nichrome, or similar heatable materials, and may have any suitable cross-sectional shape including, for example, round, oval, oblong, flat, or polygon. In some embodiments, the heating wire is insulated; in other embodiments the heating wire is uninsulated. In some embodiments, direct heating element 24 has a helical/spiral or coil shape which may be formed, for example, by winding the heating wire around the control member 50 two or more times (e.g., twice, thrice, about four times, about 5 times, about 10 times, about 15 times, about 20 times, about 25 times, about 30 times, about 35 times, about 40 times, about 45 times, about 50 times, or more than about 50 times). In some embodiments, for example where the heating wire is uninsulated, the direct heating element 24 has a helical/spiral or coil shape in which successive loops of the direct heating element 24 are separated such that they do not contact each other in the deployed state (e.g., a sufficiently large pitch between each loop). Such embodiments are particularly advantageous when the occlusion element 19 is to be inflated by introducing air or another non-conductive gas into the occlusion element 19 because individual windings of the direct heating element 24 may be equally spaced apart along the length of the control member 50. In other embodiments, however, the number, arrangement, and/or composition of the direct heating element 24 may vary.

The occlusion element 19 is adapted for expansion or inflation between a low-profile configuration (e.g., a collapsed or deflated shape) suitable for passage through the vasculature and an expanded configuration (e.g., a therapeutic or inflated shape) configured to press against the inner surface of the wall of a renal artery. In some embodiments, the occlusion element 19 is sized to occlude or substantially occlude the renal artery when in the expanded configuration. The direct heating element 24 is contained within the occlusion element 19, but the direct heating element 24 is not necessarily secured to or otherwise attached to the occlusion element 19. The occlusion element 19, for example, can be a balloon or other structure, such as a basket made from a fine mesh or braided material, sized and shaped such that when expanded at least a portion of the outer surface of the occlusion element 19 directly contacts the inner wall of the renal artery. The occlusion element 19 may be a compliant balloon, a non-compliant balloon, or a semi-compliant balloon. Accordingly, the expandable balloon may comprise any suitable material or components including, for example, silicone, latex, polyurethane, thermoplastic elastomers, nylon, polyethylene terephthalate (PET), and the like.

Similarly, the control member 50 and the direct heating element 24 are configured to be delivered through the vasculature to a renal blood vessel (e.g., a renal artery) in a low-profile state (e.g., a generally straight shape) and expand radially outward to an expanded state in which the direct heating element 24 has a generally spiral/helical configuration. In some embodiments, the occlusion element 19 is a balloon configured to be inflated with a fluid, such as saline, contrast fluid, or a mixture thereof. In such embodiments, the control member 50 additionally includes one or more fluid ports configured to allow influx of the fluid into the balloon. In other embodiments, the expandable balloon is configured to be inflated with a gas, such as air or carbon dioxide or the like, or a combination thereof. In such embodiments, the control member 50 additionally includes one or more gas ports configured to allow influx of the gas into the balloon.

Alternatively, the control member 50 and the direct heating element 24 may have a non-helical shape. In some embodiments, the direct heating element 24 may be a ring, such as a slanted ring. The therapeutic assembly 21 may be self-expanding, manually expandable (e.g., via a remote actuator), or transformed between the low-profile and expanded states using other mechanisms or techniques. Once in the deployed state, system 10 may provide therapeutically-effective thermally-induced renal neuromodulation by delivering thermal energy at the target therapeutic site through the direct heating element 24.

In some alternate embodiments, the therapeutic assembly 21 does not include an occlusion element 19. In such embodiments, the control member 50 and the direct heating element 24 may not be housed inside another component and the direct heating element 24 may directly contact the inner surface of the wall of the renal blood vessel (e.g., a renal artery) in the expanded configuration.

The catheter 12 can also include an atraumatic tip 40 extending from a distal end of the therapeutic assembly 21. The atraumatic tip 40 can include a distal opening for a guide wire and optionally one or more radiopaque markers. The atraumatic tip 40 may be made from any suitable material, for example a polyether block amide copolymer (e.g., sold under the trademark PEBAX), a thermoplastic polyether urethane material (sold under the trademark ELASTHANE or PELLETHANE), or other suitable materials having the desired properties, including a selected durometer. In one particular embodiment, for example, about 5 to 30 weight percent of siloxane can be blended with the tip material (e.g., the thermoplastic polyether urethane material), and electron beam or gamma irradiation may be used to induce cross-linking of the materials. In other embodiments, the atraumatic tip 40 may be formed from different material(s) and/or have a different arrangement. The atraumatic tip 40 can be affixed to the distal end of the therapeutic assembly 21 via adhesive, crimping, over-molding, or other suitable techniques.

In some embodiments, the distal end of the therapeutic assembly 21 may also be configured to engage another element of the system 10 or catheter 12. For example, the distal end of the therapeutic assembly 21 may define a passageway for receiving a guide wire (not shown) for delivery of the treatment device using over-the-wire ("OTW") or rapid exchange ("RX") techniques. Further details regarding such arrangements are described below.

The catheter 12 can also include a cable 28 that electrically couples the thermal energy generator 26 to the direct heating element 24, and the system 10 can include a control mechanism 32, such as a foot pedal or handheld remote control device, connected to the thermal energy generator 26 to allow the clinician to initiate, terminate and, optionally, adjust various operational characteristics of the energy generator 26, including, but not limited to, power delivery. The remote control device (not shown) can be positioned in a sterile field and operably coupled to the thermal energy generator 26, and can be configured to allow the clinician to selectively activate and deactivate the direct heating element 24.

The thermal energy generator 26 can be configured to deliver the treatment energy via an automated control algorithm 30 and/or under the control of a clinician. For example, the thermal energy generator 26 can include computing devices (e.g., personal computers, server computers, tablets, etc.) having processing circuitry (e.g., a microprocessor) that is configured to execute stored instructions relating to the control algorithm 30. In addition, the processing circuitry may be configured to execute one or more evaluation/feedback algorithms 31, which can be communicated to the clinician. For example, the thermal energy generator 26 can include a monitor or display 33 and/or associated features that are configured to provide visual, audio, or other indications of power levels, sensor data, and/or other feedback. The thermal energy generator 26 can also be configured to communicate the feedback and other information to another device, such as a monitor in a catheterization laboratory. The thermal energy generator 26 can have a variety of suitable power-supply configurations. For example, the thermal energy generator 26 can include a power adapter (e.g., a plug configured to fit into a standard power receptacle or a receptacle of an external power-supply unit) and a power cord electrically connected to the thermal energy generator 26. In other embodiments, the thermal energy generator 26 can be configured to receive power from a battery, such as a rechargeable battery within a pack removably connectable to the thermal energy generator 26.

In several embodiments, the thermal energy generator 26 may include a radio-frequency identification (RFID) evaluation module (not shown) mounted at or near one or more ports on the thermal energy generator 26 and configured to wirelessly mad and write to one or more RFID tags (not shown) on the catheter 12. In one particular embodiment, for example, the catheter 12 may include an RFID tag housed within or otherwise attached to the connector portion of the cable 28 that is coupled to the energy generator 26. The RFD tag can include, for example, an antenna and an RFID chip for processing signals, sending/receiving RF signals, and storing data in memory. Suitable RFID tags include, for example, MB89R118 RFID tags available from Fujitsu Limited of Tokyo, Japan. The memory portion of the RFID tag can include a plurality of blocks allocated for different types of data. For example, a first memory block can include a validation identifier (e.g., a unique identifier associated with the specific type of catheter and generated from the unique ID of the RFID tag using an encrypting algorithm), and a second memory block can be allocated as a catheter usage counter that can be read and then written to by the RFID module carried by the energy generator 26 after catheter use. In other embodiments, the RFID tag can include additional memory blocks allocated for additional catheter usage counters (e.g., to allow the catheter 12 to be used a specific limited number of times) and/or other information associated with the catheter 12 (e.g., lot number, customer number, catheter model, summary data, etc.).

The RFID evaluation module at the thermal energy generator 26 can include an antenna and a processing circuit that are together used to communicate with one or more portions of the thermal energy generator 26 and wirelessly read/write to one or more RFID tags within its proximity (e.g., when the cable 28 with an RFID tag is attached to the thermal energy generator 26). Suitable RFID evaluation modules include, for example, a TRF7960A Evaluation Module available from Texas Instruments Incorporated of Dallas, Texas.

In operation, the RFID evaluation module is configured to read information from the RFID tag (carried by the cable 28 or another suitable portion of the catheter 12), and communicate the information to software of the thermal energy generator 26 to validate the attached catheter 12 (e.g., validate that the catheter 12 is compatible with the thermal energy generator 26), read the number of previous uses associated with the particular catheter 12, and/or write to the RFID tag to indicate catheter use. In various embodiments, the thermal energy generator 26 may be configured to disable energy delivery to the catheter 12 when predefined conditions of the RFID tag are not met. For example, when the catheter 12 is connected to the thermal energy generator 26, the RFID evaluation module can read a unique anti-counterfeit number in an encrypted format from the RFID tag, decrypt the number, and then authenticate the number and the catheter data format for recognized catheters (e.g., catheters that are compatible with the particular thermal energy generator 26, non-counterfeit catheters, etc.). In various embodiments, the RFID tag can include identifier(s) that correspond to a specific type of catheter, and the RFID evaluation module can transmit this information to a main controller of the thermal energy generator 26, which can adjust the settings (e.g., the control algorithm 30) of the thermal energy generator 26 to the desired operating parameters/characteristics (e.g., power levels, display modes, etc.) associated with the specific catheter. Further, if the RFID evaluation module identifies the catheter 12 as counterfeit or is otherwise unable to identify the catheter 12, the thermal energy generator 26 can automatically disable the use of the catheter 12 (e.g., preclude energy delivery).

Once the catheter 12 has been identified, the RFID evaluation module can read the RFID tag memory address spaces to determine if the catheter 12 was previously connected to a generator (i.e., previously used). In certain embodiments, the RFID tag may limit the catheter 12 to a single use, but in other embodiments the RFID tag can be configured to provide for more than one use (e.g., 2 uses, 5 uses, 10 uses, etc.). If the RFID evaluation module recognizes that the catheter 12 has been written (i.e., used) more than a predetermined use limit, the RFID module can communicate with the thermal energy generator 26 to disable energy delivery to the catheter 12. In certain embodiments, the RFID evaluation module can be configured to interpret all the catheter connections to an energy source within a predefined time period (e.g., 5 hours, 10 hours, 24 hours, 30 hours, etc.) as a single connection (i.e., a single use), and allow the catheter 12 to be used multiple times within the predefined time period. After the catheter 12 has been detected, recognized, and judged as a "new connection" (e.g., not used more than the predefined limit), the RFID evaluation module can write to the RFID tag (e.g., the time and date of the system use and/or other information) to indicate that the catheter 12 has been used. In other embodiments, the RFID evaluation module and/or RFID tag may have different features and/or different configurations.

The system 10 can also include one or more sensors 29 located proximate to, distal to, or within the direct heating element 24. For example, the system 10 can include temperature sensors (e.g., thermocouple, thermistor, etc.), impedance sensors, pressure sensors, optical sensors, flow sensors, and/or other suitable sensors connected to one or more supply wires (not shown) that transmit signals from the sensors and/or convey energy to the direct heating element 24.

Figure 2:
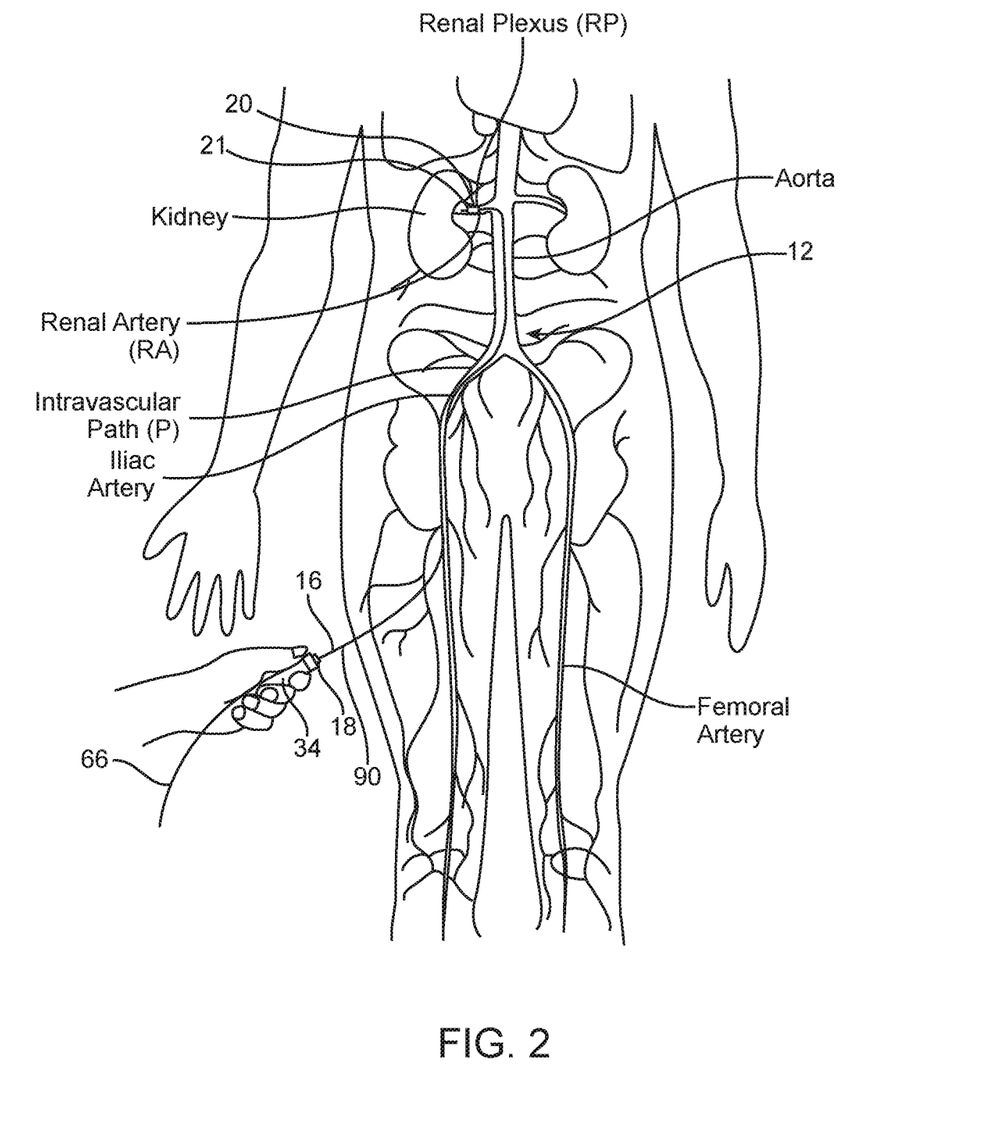
FIG. 2 illustrates modulating renal nerves with a catheter configured in accordance with an embodiment of the present technology.

FIG. 2 (with additional reference to FIG. 1) illustrates modulating renal nerves with an embodiment of the system 10. The catheter 12 is configured to access the renal plexus RP through an intravascular path P, such as a percutaneous access site in the femoral (illustrated), brachial, radial, or axillary artery to a targeted treatment site within a respective renal artery RA. As illustrated, a section of the proximal portion 18 of the shaft 16 is exposed externally of the patient. By manipulating the proximal portion 18 of the shaft 16 from outside the intravascular path P, the clinician may advance the shaft 16 through the sometimes tortuous intravascular path P and remotely manipulate the distal portion 20 of the shaft 16. In the embodiment illustrated in FIG. 2, the therapeutic assembly 21 is delivered intravascularly to the treatment site using a guide wire 66 in an OTW technique. As noted previously, the distal end of the therapeutic assembly 21 may define a lumen or passageway for receiving the guide wire 66 for delivery of the catheter 12 using either OTW or RX techniques. At the treatment site, the guide wire 66 can be at least partially axially withdrawn or removed, and the therapeutic assembly 21 can transform or otherwise be moved to a deployed state for delivering energy at the treatment site. Further details regarding such arrangements are described below with reference to FIGS. 3A and 3B. The guide wire 66 may comprise any suitable medical guide wire sized to slidably fit within the lumen. In one particular embodiment, for example, the guide wire 66 may have a diameter of 0.356 mm (0.014 inch). In other embodiments, the therapeutic assembly 21 may be delivered to the treatment site within a guide sheath (not shown) with or without using the guide wire 66. When the therapeutic assembly 21 is at the target site, the guide sheath may be at least partially withdrawn or retracted and the therapeutic assembly 21 can be transformed into the deployed state. Additional details regarding this type of configuration are described below. In still other embodiments, the shaft 16 may be steerable itself such that the therapeutic assembly 21 may be delivered to the treatment site without the aid of the guide wire 66 and/or guide sheath.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the therapeutic assembly 21. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the catheter 12. Further, in some embodiments, image guidance components (e.g., IVUS, OCT) may be integrated with the catheter 12 and/or run in parallel with the catheter 12 to provide image guidance during positioning of the therapeutic assembly 21. For example, image guidance components (e.g., IVUS or OCT) can be coupled to the therapeutic assembly 21 (e.g., proximal to the therapeutic arms) to provide three-dimensional images of the vasculature proximate the target site.

The purposeful application of thermal energy from the direct heating element 24 may then be applied to target tissue to induce one or more desired neuromodulating effects on localized regions of the renal artery and adjacent regions of the renal plexus RP, which lay intimately within, adjacent to, or in close proximity to the adventitia of the renal artery RA. The purposeful application of the thermal energy may achieve neuromodulation along all or at least a portion of the renal plexus RP. The neuromodulating effects are generally a function of, at least in part, power, time, contact between the direct heating element 24 (FIG. 1) and the vessel wall, optionally separated by an occlusion element 19, and blood flow (if any) through the vessel. The neuromodulating effects may include denervation, thermal ablation, and/or non-ablative thermal alteration or damage (e.g., via sustained heating and/or resistive heating). In some embodiments, thermal energy from the direct heating element 24 is sufficient to cause at least partial renal denervation in the patient. In some embodiments, thermal energy from the direct heating element 24 is sufficient to cause at least partial ablation of at least one renal nerve of the patient. Desired thermal heating effects may include raising the temperature of target neural fibers above a predetermined threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for ablative thermal alteration.

Figure 3A:
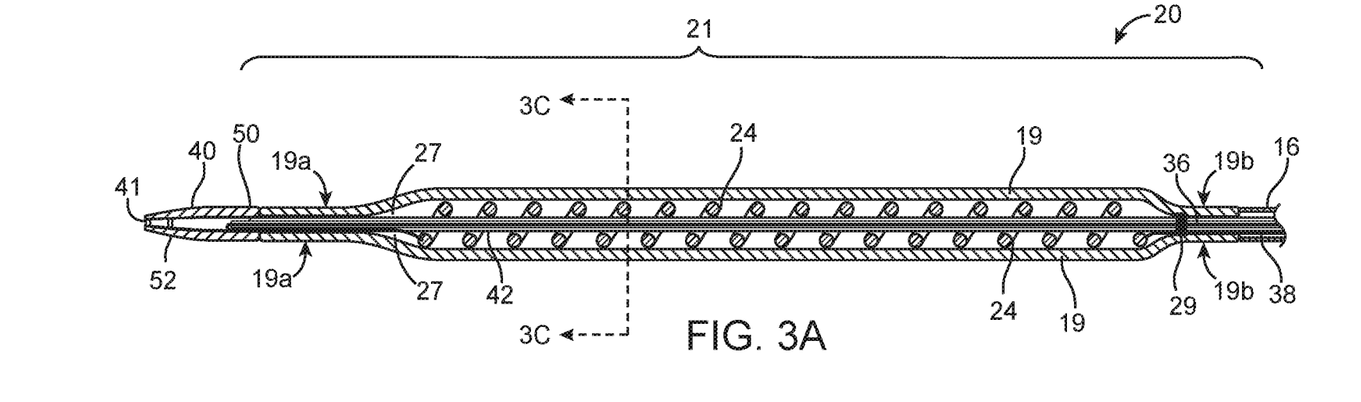
FIG. 3A is a side view of a distal portion of a catheter having a therapeutic assembly in a delivery state outside a patient in accordance with an embodiment of the present technology.
Figure 3B:
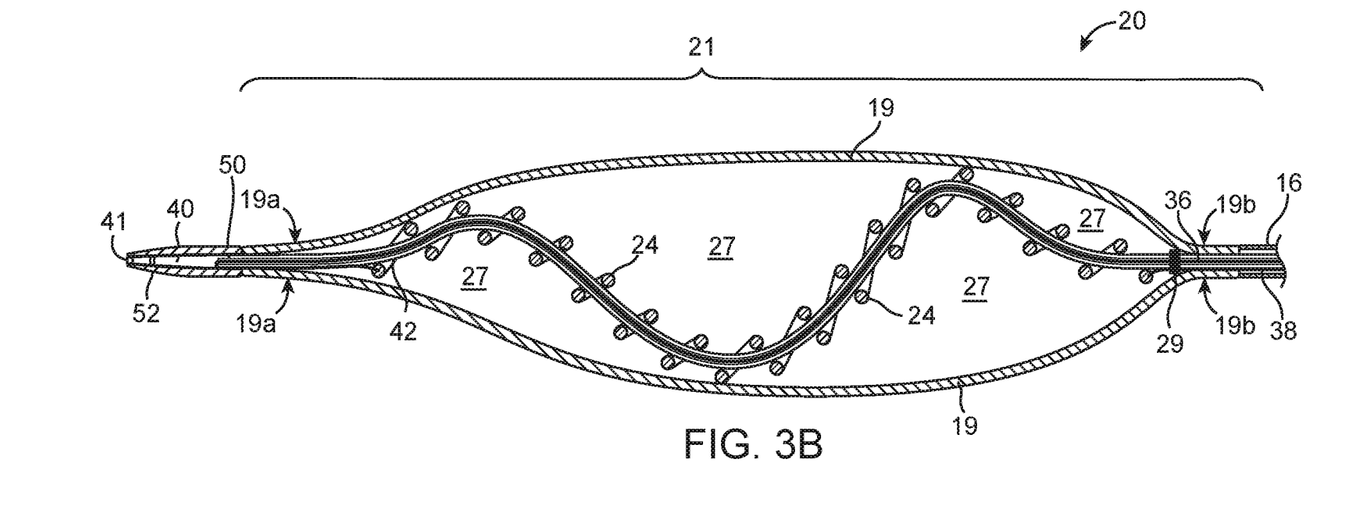
FIG. 3B is a side view of a distal portion of a catheter having a therapeutic assembly in a deployed state outside a patient in accordance with an embodiment of the present technology.
Figure 3C:
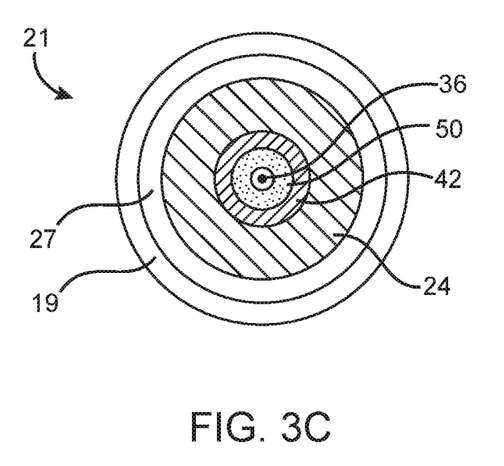
FIG. 3C is a cross-sectional view the catheter of FIG. 3A in a delivery state in accordance with an embodiment of the present technology.

FIG. 3A is a side view of the distal portion 20 of the shaft 16 and the therapeutic assembly 21 in the delivery state outside a patient; FIG. 3B is a side view of the distal portion 20 of the shaft 16 and the therapeutic assembly 21 in the deployed state outside a patient; and FIG. 3C is a perspective view of the therapeutic assembly 21 in the deployed state outside the patient.

As best seen in FIGS. 3A and 3B, the therapeutic assembly 21 includes the control member 50 and at least one direct heating element 24. In this embodiment, the therapeutic assembly 21 also includes a flexible tube 42 having a lumen disposed between the pre-shaped control member 50 and the direct heating element 24. The flexible tube 42 may be composed of a polymer material such as polyamide, polyimide, polyether block amide copolymer sold under the trademark PEBAX, polyethylene terephthalate (PET), polypropylene, aliphatic, polycarbonate-based thermoplastic polyurethane sold under the trademark CARBOTHANE, or a polyether ether ketone (PEEK) polymer that provides the desired flexibility. In other embodiments, however, the tube 42 may be composed of other suitable materials, for example to offer electrical insulation between the direct heating element 24 and the control member 50. In other embodiments, the tube 42 is absent and the direct heating element 24 is in contact with the control member 50.

The therapeutic assembly 21 may also include one or more sensors 29. The sensors 29 may be any suitable type of sensor including, for example, a thermocouple. The sensor 29 may be configured to monitor the temperature or change in temperature of the direct heating element 24. The sensor 29 may be configured to detect the temperature or change in temperature of tissue, for example, wall of the renal vessel (e.g., renal artery). In such an embodiment, the sensor 29 is positioned to contact the tissue, for example, wherein at least a portion of the sensor 29 is directly exposed to the tissue. In some embodiments, the sensors 29 include more than one type of sensor for monitoring more than one type of parameter. The sensors 29 may be located at any suitable location in the therapeutic assembly 21 depending on the type of sensor employed and the parameter to be monitored. Sensor 29 is shown in FIG. 3A in a representative fashion located within the occlusion element 19, but sensor 29 can be located at any suitable location of the therapeutic assembly 21 including, for example, outside of the occlusion element 19.

Referring to FIG. 3B, one embodiment of the control member 50 has a pre-set spiral/helical shape that defines the expanded state of the control member 50 when the therapeutic assembly 21 is in the deployed state. The control member 50 can be straightened by inserting a guidewire or other element through the lumen of the control member 50 to shape the control member 50 in the low-profile state. The control member 50 may be arranged in a single or dual-layer configuration, and may be manufactured with a selected tension, compression, torque and pitch direction. The control member 50 can be formed of any suitable material, including materials comprising polymers, metals, alloys, or a combination thereof. For example, in one embodiment the control member 50 comprises a nitinol multifilar stranded wire wound to create a tube with a lumen therethrough, such as that sold under the trademark HELICAL HOLLOW STRAND (HHS), and commercially available from Fort Wayne Metals of Fort Wayne, Indiana.

In operation, a guidewire or other element is inserted in the lumen of the control member 50 to straighten the control member 50 and the direct heating element 24 so that the therapeutic assembly 21 is in the delivery state shown in FIG. 3A. After the therapeutic assembly 21 is positioned at a target site in the renal artery, the occlusion element 19 is expanded to contact the inner surface of the wall of the renal artery and the guidewire is withdrawn. Without the guidewire, the pre-shaped control member 50 moves toward its pre-formed shape, such as a spiral/helical shape, which in turn causes the direct heating element 24 to have a shape set by the pre-formed shape of the control member 50. As best seen in FIG. 3B, for example, in one embodiment the direct heating element 24 has a helical/spiral shape in the expanded state such that the direct heating element 24 contacts an inner surface of the occlusion element 19. With the outer surface of the occlusion element 19 positioned in stable apposition with the wall of the renal artery (FIG. 2), the direct heating element 24 is heated to transfer heat through the occlusion element to the renal nerves for treatment.

Forming the control member 50 of nitinol multifilar stranded wire(s) or other similar materials is expected to eliminate the need for any additional reinforcement wire(s) or structures within the therapeutic assembly 21 to provide a desired level of support and rigidity to the therapeutic assembly 21. This feature is expected to reduce the number of manufacturing processes required to form the catheter 12 and reduce the number of materials required for the device. Another feature of the therapeutic assembly 21 is that the control member 50 and inner wall of the tube 42, when present, may be in intimate contact such that there is little or no space between the control member 50 and the tube 42. In one embodiment, for example, the tube 42 can be expanded prior to assembly such that applying hot air to the tube 42 during the manufacturing process can shrink the tube onto the control member 50, as will be understood by those familiar with the ordinary use of shrink tubing materials. This feature is expected to inhibit or eliminate wrinkles or kinks that might occur in the tube 42 as the therapeutic assembly 21 transforms from the relatively straight delivery state to the generally helical deployed state.

In other embodiments, the control member 50 and/or other components of the therapeutic assembly 21 may be composed of different materials and/or have a different arrangement. For example, the control member 50 may be formed from other suitable shape memory materials (e.g., wire or tubing besides HHS, shape memory polymers, electro-active polymers) that are pre-formed or pre-shaped into the desired expanded state. Alternatively, the control member 50 may be formed from multiple materials such as a composite of one or more polymers and metals.

As shown in FIGS. 3A-3B, occlusion element 19 can include a distal portion 19a that is secured distally near the distal end of the control member 50, and a proximal portion 19b that is secured to the proximal end of the control member 50. Alternatively, the occlusion element 19 can include a distal portion 19a that is secured to the distal end of the control member 50, and a proximal portion 19b that is secured to the shaft 16. Thus, the occlusion element 19 defines an intra-occlusion element space 27 that can be filled with a fluid such as a gas (e.g., air and/or carbon dioxide) or a liquid (e.g., saline, contrast fluid, or a mixture thereof).

Figure 3D:
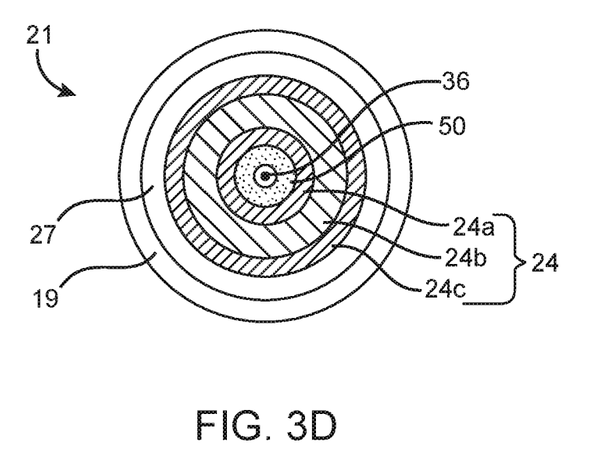
FIG. 3D is a cross-sectional view of a catheter in a delivery state in accordance with another embodiment of the present technology.

The direct heating element 24 is electrically connected to the energy generator 26 by wires 36 and 38. As shown in FIGS. 3C-3D, wire 36 extends through the control member 50 and connects to the distal end of the direct heating element 24. Wire 38 is outside tube 42 and connects to the proximal end of direct heating element 24. Wires 36 and 38 may alternatively be housed in any other suitable location in order to provide reliable electrical contact with the direct heating element 24. For example, wire 36 may be outside tube 42, and/or wire 38 may be inside tube 42.

FIG. 3C shows a cross-sectional view of the therapeutic assembly 21 of FIG. 3A. The control member 50 is a hollow tube as described above, and includes wire 36. The tube 42 surrounds the control member 50 and insulates the control member 50 from the direct heating element 24. Occlusion element 19 surrounds the direct heating element 24. In an alternative embodiment, shown in similar cross-section in FIG. 3D, wire 36 runs inside control member 50. The direct heating element comprises a heating wire 24b surrounded by insulation layers 24a and 24c. Insulation layer 24a is in direct contact with the control member 50 and electrically isolates the control member 50 from the heating wire 24b. Accordingly, tube 42 is not needed to isolate the direct heating element 24 from the control element 50. One of skill in the art will readily understand that insulation layers 24a and 24c may be continuous depending on the shape and configuration of the direct heating element 24. The occlusion element 19 surrounds the direct heating element 24.

Figure 4:
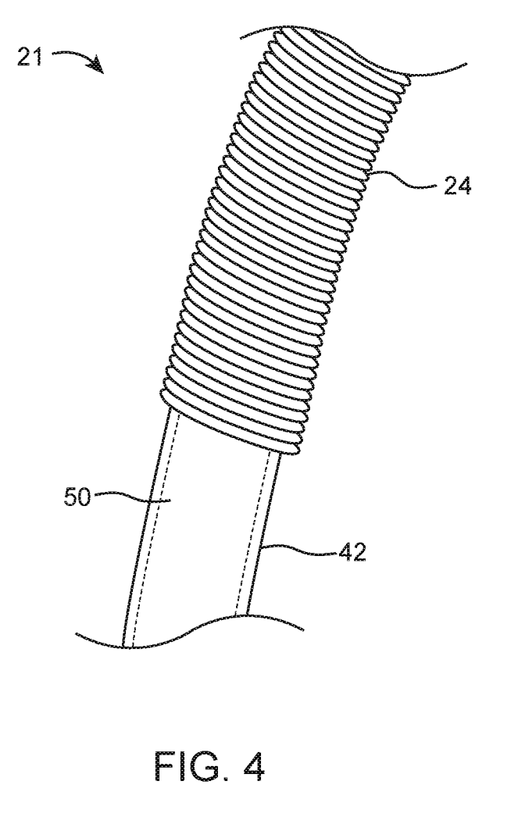
FIG. 4 is a perspective view of a portion of a therapeutic assembly having a direct heating element having a spiral or coil shape in accordance with an embodiment of the present technology.
Figure 5:
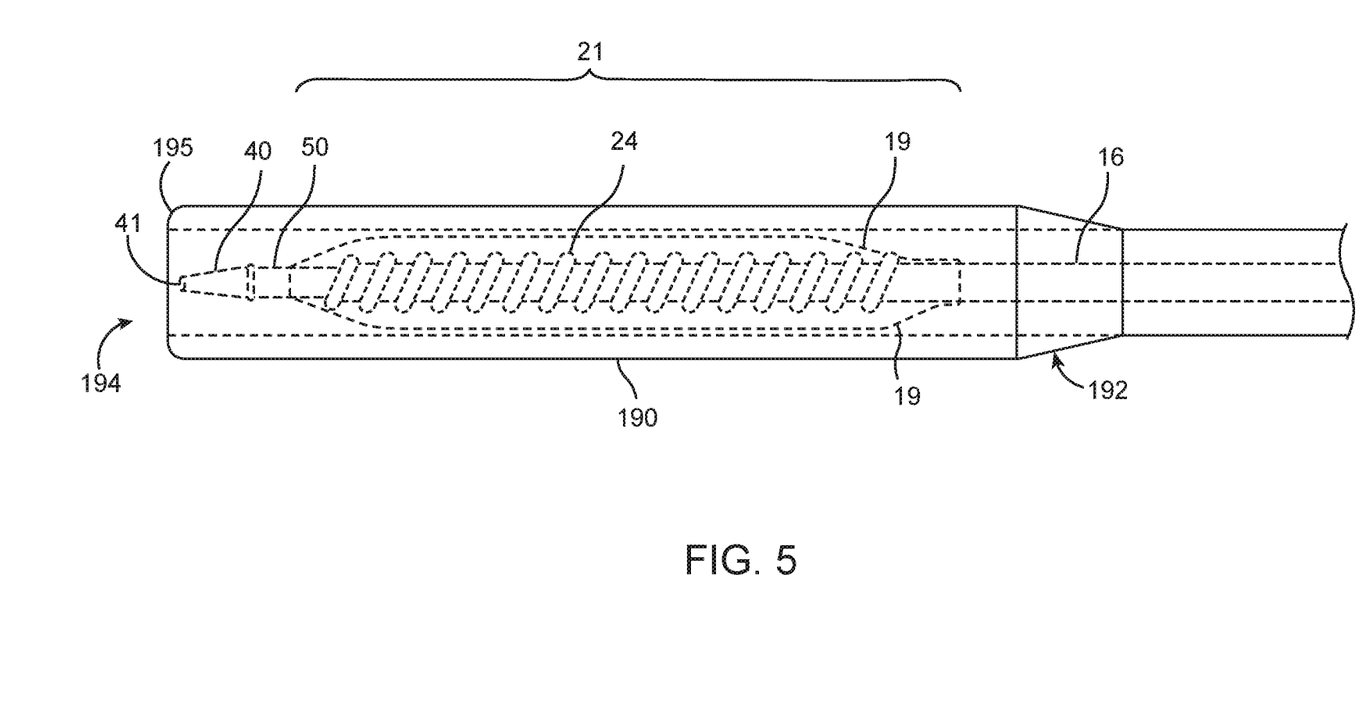
FIG. 5 is a partially schematic side view of a loading tool configured in accordance with an embodiment of the present technology.

FIG. 4 is an enlarged view of a portion of the catheter 12 of FIGS. 3A-3B. Referring to FIGS. 1, 3A-3B and 4 together, as noted above, the tube 42 is configured to fit tightly against the control member 50 to minimize the space between an inner portion of the tube 42 and the components positioned therein. This may, for example, help prevent the formation of wrinkles in the therapeutic assembly 21 during deployment. In the embodiment shown in FIG. 4, the direct heating element 24 includes a single insulated heating wire wrapped around tube 42 to form a coil such that successive loops of the coil are in contact with each other or substantially in contact with each other. In other embodiments, for example as shown in FIG. 5, the direct heating element includes a heating wire wrapped around the control member 50 to form a coil such that successive loops of the coil are not in contact with each other. In such embodiments, the heating wire may be insulated or, if the control member 50 is non-conductive and intra-occlusion element space 27 will not include a conductive fluid, the heating wire may be uninsulated.

In operation (and with reference to FIGS. 2, 3A, 3B and 3C), after the therapeutic assembly 21 has been positioned at a desired location within the renal artery RA of the patient, the therapeutic assembly 21 may be transformed from the delivery state to the deployed state. The transformation may be initiated using an arrangement of device components as described herein with respect to the particular embodiments and their various modes of deployment. In one embodiment, for example, the therapeutic assembly 21 may be deployed by retracting the guide wire 66 (FIG. 2) until a distal tip of the guide wire 66 is generally aligned with the tip 40 of the catheter 12. In some embodiments, the guide wire 66 may have a varying stiffness or flexibility along its length (e.g., to provide increased flexibility distally). In certain embodiments, the guide wire 66 may be completely withdrawn from the shaft 16. Alternatively, the guide wire 66 may be partially withdrawn from the shaft 16, for example, completely withdrawn from the therapeutic assembly 21 but at least partially remaining within the shaft 16. In some embodiments, complete or partial withdrawal of the guide wire 66 from the therapeutic assembly 21 induces the therapeutic assembly 21 to transform (e.g., automatically transform) into the deployed state. Deployment of the therapeutic assembly 21 may additionally or alternatively be accomplished by introducing a fluid, such as a gas (e.g., air) or a liquid (e.g., saline, contrast fluid, or a mixture thereof) into the intra-occlusion element space 27 of occlusion element 19.

In some embodiments, the guide wire 66 may have a stiffness profile that permits the distal portion of the guide wire 66 to remain extended from the opening 41 while still permitting the therapeutic assembly 21 to transform to the deployed state, for example upon introduction of a fluid such as a gas (e.g., air) or a liquid (e.g., saline, contrast fluid, or a mixture thereof) into intra-occlusion element space 27 of occlusion element 19. In still other embodiments, the guide wire 66 may be withdrawn completely from the therapeutic assembly 21 (e.g., a distal-most end portion of the guide wire 66 is proximal of the therapeutic assembly 21) to permit the transformation, while a distal-most portion of the guide wire 66 remains within the shaft 16. In yet another embodiment, the guide wire 66 may be withdrawn completely from the shaft 16. In any of the foregoing examples, the clinician can withdraw the guide wire 66 sufficiently to observe transformation of the therapeutic assembly 21 to the deployed state and/or until an X-ray image shows that the distal tip of the guide wire 66 is at a desired location relative to the therapeutic assembly 21 (e.g., generally aligned with the tip 40, completely withdrawn from the therapeutic assembly 21, etc.). In some embodiments, the extent of withdrawal for the guide wire 66 can be based, at least in part, on the clinician's judgment with respect to the selected guide wire and the extent of withdrawal necessary to achieve deployment.

After treatment, the therapeutic assembly 21 may be transformed into a low-profile state for removal or repositioning by withdrawing the gas or liquid from the intra-occlusion element space 27 and/or axially advancing the guide wire 66 relative to the therapeutic assembly 21. In one embodiment, for example, the guide wire 66 may be advanced until the distal tip of the guide wire 66 is generally aligned with the tip 40, and the catheter 12 can then be pulled back over the stationary guide wire 66. In other embodiments, however, the distal-most portion of the guide wire 66 may be advanced to a different location relative to the therapeutic assembly 21 to achieve transformation of the therapeutic assembly 21 back to the delivery state.

The embodiments of the catheter systems described above include a procedural guide wire to guide the catheter to the treatment site and also to restrain the therapeutic assembly in the delivery state. In further embodiments, catheter systems configured in accordance with the present technology may further include a loading tool. For example, catheter systems configured according to the present disclosure may include an external loading tool that can be disposed and retracted over the therapeutic assembly to further assist with transforming the therapeutic assembly between the delivery and deployed states. Alternatively, catheter systems configured according to the present disclosure may include an internal loading tool disposed within the therapeutic assembly to further assist with transforming the therapeutic assembly between the delivery and deployed states.

FIG. 5, for example, is a partially schematic side view of an external loading tool 190 in accordance with an embodiment of the present technology. The loading tool 190 is a tubular structure configured to slidably move along an outer surface of the shaft 16 and the therapeutic assembly 21 (for purposes of illustration, the therapeutic assembly 21 and associated features are shown in broken lines). The loading tool 190 has a size and stiffness suitable for maintaining the therapeutic assembly 21 in the delivery state for backloading of the guide wire 66 (FIG. 2), i.e., insertion of the proximal end of guide wire 66 into the distal opening 41. In the illustrated embodiment, the loading tool 190 can include a tapered portion 192 to guide the sheath over the therapeutic assembly 21 and the associated direct heating element 24. In some embodiments, a distal portion 194 of the loading tool 190 may also include smooth, rounded inner and outer edges 195 to guide the inner wall of the loading tool over the occlusion element 19 during advancement of the loading tool relative to the therapeutic assembly 21. The loading tool 190 may be composed of high-density polyethylene (HDPE) or other suitable materials having a desired strength and lubricity. In still other embodiments, the loading tool 190 may be composed of two or more different materials. In one embodiment, for example, the larger diameter section of the loading tool 190 distal of the tapered portion 192 may be composed of HDPE, while the smaller diameter section of the loading tool 190 proximal of the tapered portion 192 may be composed of linear low-density polyethylene (LLDPE). In still further embodiments, the loading tool 190 may be composed of different materials and/or have a different arrangement.

In some embodiments, the loading tool 190 may be used in conjunction with the catheter 12 while the catheter 12 is external to the patient before treatment, and then the loading tool 190 may be removed from the catheter 12 before the catheter 12 is inserted into the patient. More specifically, as discussed above, the loading tool 190 can be used to maintain the therapeutic assembly 21 in the delivery state while the guide wire is backloaded (moving from a distal end toward a proximal end of the catheter 12). The loading tool 190 can then be removed from the catheter 12, and the therapeutic assembly 21 can be restrained in the delivery state with the support of the guide wire. In another embodiment, the loading tool 190 may remain installed on the catheter 12 after backloading of the guide wire, but may slide down the length of the catheter 12 to a proximal portion 18 of the catheter 12 near the handle 34 (FIG. 1). In this way, the loading tool 190 remains with the catheter 12, but is out of the way during treatment.

In still other embodiments, however, the loading tool 190 may remain at or near the distal portion 20 (FIG. 1) of the catheter 12 during treatment. For example, in one embodiment, a clinician may keep the loading tool 190 at or near the distal portion 20 of the catheter 12 and then insert the loading tool 190 into a hemostasis valve (not shown) connected to a guide catheter (not shown). Depending upon a profile of the loading tool 190 and an inner diameter of the hemostasis valve, the clinician may be able to insert approximately 2 to 4 cm of the loading tool 190 into the hemostasis valve. One advantage of this approach is that the therapeutic assembly 21 (FIGS. 3A and 3B) is further protected as the catheter 12 is advanced through the hemostasis valve, and the clinician is expected to feel little or no friction between the catheter 12 and the hemostasis valve. In other embodiments, however, the loading tool 190 may have a different arrangement relative to the hemostasis valve and/or the other components of the system 10 (FIG. 1) during operation.

In still other embodiments, an internal loading tool comprising a relatively stiff wire may be included at or near the distal portion of the catheter 12. The internal loading tool is configured to maintain the therapeutic assembly 21 in the low-profile delivery state, e.g., during packaging or shipping. In operation, the internal loading tool may be removed from the catheter 12 and replaced with a guidewire immediately before use.

III. Additional Clinical Uses of the Disclosed Apparatuses, Methods and Systems Although much of the disclosure in this Specification relates to at least partially denervating a kidney of a patient to block afferent and/or efferent neural communication between a renal blood vessel (e.g., renal artery) and the brain, the apparatuses, methods and systems described herein may also be used for other intravascular treatments. For example, the aforementioned catheter system, or select aspects of such system, can be placed in other peripheral blood vessels to deliver energy to achieve a neuromodulatory effect by altering nerves proximate to these other peripheral blood vessels. There are a number of arterial vessels arising from the aorta which travel alongside a rich collection of nerves to target organs. Utilizing the arteries to access and modulate these nerves may have clear therapeutic potential in a number of disease states. Some examples include the nerves encircling the celiac trunk, superior mesenteric artery, and inferior mesenteric artery.

Sympathetic nerves proximate to or encircling the arterial blood vessel known as the celiac trunk may pass through the celiac ganglion and follow branches of the celiac trunk to innervate the stomach, small intestine, abdominal blood vessels, liver, bile ducts, gallbladder, pancreas, adrenal glands, and kidneys. Modulating these nerves either in whole (or in part via selective modulation) may enable treatment of conditions including (but not limited to) diabetes, pancreatitis, obesity, hypertension, obesity related hypertension, hepatitis, hepatorenal syndrome, gastric ulcers, gastric motility disorders, irritable bowel syndrome, and autoimmune disorders such as Crohn's disease.

Sympathetic nerves proximate to or encircling the arterial blood vessel known as the inferior mesenteric artery may pass through the inferior mesenteric ganglion and follow branches of the inferior mesenteric artery to innervate the colon, rectum, bladder, sex organs, and external genitalia. Modulating these nerves either in whole (or in part via selective modulation) may enable treatment of conditions including (but not limited to) (I motility disorders, colitis, urinary retention, hyperactive bladder, incontinence, infertility, polycystic ovarian syndrome, premature ejaculation, erectile dysfunction, dyspareunia, and vaginismus.

While arterial access and treatments have received attention in this Specification, the disclosed apparatuses, methods and systems can also be used to deliver treatment from within a peripheral vein or lymphatic vessel.

IV. Further Examples

The following examples are illustrative of several embodiments of the present technology:

1. A catheter apparatus, comprising:
   an elongated tubular shaft having a proximal portion and a distal portion;
   a therapeutic assembly at the distal portion of the elongated shaft and configured to be located at a target location within a renal artery of a human patient, the therapeutic assembly comprising—
      a control member (e.g., composed of a nitinol multiilar stranded wire) having a pre-formed helical shape, a tubular structure, and a lumen therethrough;
      a direct heating element carried by the control member, and
      an occlusion element at the distal portion of the elongated member in which the control member and the direct heating element are positioned.

2. The catheter apparatus of example 1 wherein the elongated tubular shaft and the therapeutic assembly together define therethrough a guide wire lumen configured to slidably receive a medical guide wire, and wherein axial movement of the guide wire relative to the therapeutic assembly transforms the control member between (a) a low-profile state and (b) an expanded state having a helical shape set by the control member.

3. The catheter apparatus of example 1 or example 2 wherein the occlusion element is selectively transformable between a low-profile configuration in a delivery state and an expanded configuration sized to fit within the renal artery in a deployed state.

4. A catheter apparatus, comprising:
   an elongated tubular shaft having a proximal portion and a distal portion;
   a therapeutic assembly disposed at the distal portion of the elongated shaft and adapted to be located at a target location within a renal artery of a human patient, the therapeutic assembly comprising—
      an occlusion element;
      a control member comprising a pre-formed helical shape, wherein the control member is a tubular structure having a lumen therethrough; and
      a direct heating element carried by the control member, wherein the control member and the direct heating element are within the occlusion element;
   wherein the therapeutic assembly is configured to provide a first, delivery state and a second, deployed state having a helical shape set by the control member; and
   wherein the control member is selectively transformable between a low-profile state in the first, delivery state and an expanded state sized to fit within the renal artery in the second, deployed state.

5. The catheter apparatus of any one of examples 1 to 4 wherein the therapeutic assembly is configured to transform between the delivery state and the deployed state while at least a distal portion of the guide wire remains in the guide wire lumen of the therapeutic assembly.
6. The catheter apparatus of any of examples 1 to 5 wherein the control member comprises a shape-recovery force sufficient to overcome a straightening force provided by a distal region of the guide wire to transform the therapeutic assembly to the deployed state.
7. The catheter apparatus of any of examples 1 to 6 wherein, in the expanded configuration, the occlusion element is sized to occlude the renal artery.
8. The catheter apparatus of any of examples 1 to 7 wherein the direct heating element is disposed about the control member.
9. The catheter apparatus of any of examples 1 to 8 wherein the direct heating element comprises wire wrapped around all or substantially all of the control member.
10. The catheter apparatus of any of examples 1 to 9 further comprising an energy generator external to the patient and electrically coupled to the direct heating element, wherein the energy generator comprises a battery.
11. The catheter apparatus of any of examples 1 to 10 wherein energy from the direct heating element is sufficient to cause at least partial renal denervation in the patient.
12. The catheter apparatus of any of examples 1 to 11 wherein energy from the direct heating element is sufficient to cause at least partial ablation of at least one renal nerve of the patient.
13. The catheter apparatus of any of examples 1 to 12 wherein the direct heating element is configured to physically contact an inner wall of the occlusion element when the occlusion element is in the expanded configuration and the therapeutic assembly is in the deployed state.
14. The catheter apparatus of any of examples 1 to 13 wherein, when the therapeutic assembly is in the deployed state, the direct heating element is configured to deliver energy through a wall of the occlusion element and an inner wall of the renal artery in a helical pattern.
15. The catheter apparatus of any of examples 1 to 14 wherein the occlusion element is an expandable balloon.
16. The catheter apparatus of example 15 wherein the expandable balloon is a semi-compliant or a non-compliant balloon.
17. The catheter apparatus of example 15 wherein the expandable balloon is a compliant balloon.
18. The catheter apparatus of any of examples 15 to 17 wherein the expandable balloon is configured to be inflated with a fluid selected from: saline, contrast fluid, and mixtures thereof.
19. The catheter apparatus of any of examples 15 to 18 wherein the expandable balloon is configured to be inflated with air.
20. The catheter apparatus of any of examples 1 to 19 wherein the occlusion element comprises a first distal end and a second proximal end, and wherein the first end and second end of the occlusion element are affixed to the control member.
21. The catheter apparatus of any of examples 1 to 19 wherein the occlusion element comprises a first distal end affixed to the control member, and a second proximal end affixed to the elongated tubular shaft.
22. The catheter apparatus of any of examples 1 to 21, further comprising one or more sensors at the distal portion of the elongated tubular shaft for monitoring and/or controlling effects of energy delivery from the direct heating element.
23. The catheter apparatus of example 22 wherein at least one of the sensors comprises a thermocouple for monitoring temperature.
24. A method for performing renal neuromodulation, the method comprising:
intravascularly delivering a catheter in a delivery state over a guide wire to a target treatment site within a renal blood vessel of a human patient and at least proximate to a renal nerve of the patient, wherein the catheter comprises—
an elongated shaft;
an occlusion element; and
a tubular structure and a direct heating element arranged about the tubular structure, wherein the tubular structure and the direct heating element are within the occlusion element;
expanding the occlusion element such that the occlusion element at least substantially occludes the renal blood vessel;
withdrawing the guide wire in a proximal direction until the catheter transforms from the delivery state to a deployed state wherein the tubular structure has a radially expanded, spiral shape configured to contact an inner wall of the occlusion element adjacent to an inner wall of the renal blood vessel; and
delivering heat via the direct heating element to inhibit neural communication along the renal nerve.
25. The method of example 24 wherein delivering heat via the direct heating element comprises producing a lesion in a spiral-shaped pattern along the renal blood vessel.
26. The method of example 24 or 25 wherein the direct heating element is a resistive heating element, and wherein delivering heat via the direct heating element comprises applying an electrical current to the resistive heating element.
27. The method of example 26 wherein applying an electrical current comprises applying sufficient electrical current to cause the resistive heating element to reach a predetermined temperature.
28. The method of any of examples 24 to 27 wherein the occlusion element comprises an expandable balloon.
29. The method of example 28 wherein expanding the occlusion element comprises inflating the expandable balloon with a fluid (e.g., air, saline, contrast and the like, or a mixture thereof).
30. The method of example 26, further comprising measuring a temperature of the resistive heating element during treatment and adjusting the power applied to the resistive heating element to achieve a desired temperature.
31. The method of example 24 wherein delivering heat via the direct heating element comprises delivering energy to the direct heating element to increase its temperature to a determined temperature or to a temperature within a determined range of temperatures for a period of time.
32. The method of example 31 wherein the period of time is determined based on the temperature range.

33. The method of any of examples 24 to 32 wherein delivering heat via the direct heating element to inhibit neural communication along the renal nerve comprises ablating the renal nerve.

34. The method of any of examples 24 to 33 wherein delivering heat via the direct heating element to inhibit neural communication along the renal nerve comprises partially ablating the renal nerve.

35. The method of any of examples 24 to 34 wherein delivering heat via the direct heating element to inhibit neural communication along the renal nerve comprises at least partially denervating a kidney of the patient.

36. The method of any of examples 24 to 35 further comprising monitoring a parameter of the catheter and/or tissue within the patient before and during delivery of heat via the direct heating element.

37. The method of example 36 wherein monitoring a parameter comprises monitoring temperature of the tissue and/or the temperature of the direct heating element, and wherein the method further comprises maintaining the tissue and/or the direct heating element at a desired temperature during delivery of heat via the direct heating element.

38. The method of example 35, further comprising altering delivery of the heat in response to the monitored parameter.

V. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but that well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A method for performing renal neuromodulation, the method comprising:
   intravascularly delivering a catheter comprising an occlusion element, a control member, and a neuromodulation element arranged about the control member in a low-profile delivery state to a target treatment site within a renal blood vessel of a patient, the control member and the neuromodulation element being within the occlusion element;
   expanding the occlusion element to substantially occlude the renal blood vessel;
   radially expanding the control member to place the neuromodulation element in contact with an inner wall of the occlusion element adjacent to an inner wall of the renal blood vessel, wherein the control member defines a helical shape, a spiral shape, or a ring shape when radially expanded; and
   delivering neuromodulation energy via the neuromodulation element to inhibit neural communication along the renal nerve.

2. The method of claim 1, wherein the neuromodulation element is a direct heating element, wherein the direct heating element is a resistive heating element, and wherein delivering the neuromodulation energy includes delivering heat by applying an electrical current to the resistive heating element to deliver the heat.

3. The method of claim 2, further comprising measuring a temperature of the resistive heating element during treatment and adjusting the electrical current applied to the resistive heating element to achieve a desired temperature.

4. The method of claim 2, wherein applying the electrical current to the resistive heating element includes delivering the electrical current to increase a temperature of the resistive heating element to a determined temperature or to a temperature within a determined range of temperatures for a period of time.

5. The method of claim 4, wherein the period of time is determined based on the range of temperatures.

6. The method of claim 1, wherein the occlusion element comprises an expandable balloon.

7. The method of claim 6, wherein expanding the occlusion element includes inflating the expandable balloon with a fluid selected from: air, saline, contrast, and mixtures thereof.

8. The method of claim 1, wherein delivering the neuromodulation energy to inhibit neural communication along the renal nerve comprises at least partially ablating the renal nerve.

9. The method of claim 1, further comprising monitoring a parameter of the catheter or tissue within the patient before and during delivery of the neuromodulation energy.

10. The method of claim 9, wherein monitoring the parameter includes monitoring temperature of the neuromodulation element.

11. The method of claim 9, further comprising altering delivery of the neuromodulation energy in response to the monitored parameter.

12. A method for performing renal neuromodulation, the method comprising:
   intravascularly delivering a catheter comprising an occlusion element, a tubular structure, and a direct heating element arranged about the tubular structure in a low-profile delivery state over a guide wire to a target treatment site within a renal blood vessel of a patient, the tubular structure and the direct heating element being within the occlusion element;

expanding the occlusion element to substantially occlude the renal blood vessel;

withdrawing the guide wire in a proximal direction until the tubular structure radially expands into a spiral shape to contact an inner wall of the occlusion element adjacent to an inner wall of the renal blood vessel; and delivering heat via the direct heating element to inhibit neural communication along the renal nerve.

13. The method of claim 12, wherein the direct heating element is a resistive heating element, and wherein delivering the heat includes applying an electrical current to the resistive heating element to deliver the heat.

14. The method of claim 13, further comprising measuring a temperature of the resistive heating element during treatment and adjusting the electrical current applied to the resistive heating element to achieve a desired temperature.

15. The method of claim 13, wherein applying the electrical current to the resistive heating element includes delivering the electrical current to increase a temperature of the resistive heating element to a determined temperature or to a temperature within a determined range of temperatures for a period of time.

16. The method of claim 15, wherein the period of time is determined based on the range of temperatures.

17. The method of claim 12, wherein the occlusion element comprises an expandable balloon, wherein expanding the occlusion element includes inflating the expandable balloon with a fluid selected from: air, saline, contrast, and mixtures thereof.

18. A method for performing renal neuromodulation, the method comprising:

intravascularly delivering a catheter in a low-profile delivery state over a guide wire to a target treatment site within a renal blood vessel of a patient, the catheter comprising an occlusion element, a control member, and a neuromodulation element arranged about the control member, and the control member and the neuromodulation element being within the occlusion element, wherein the guide wire is configured to hold the catheter in the low-profile delivery state when the guide wire is in a lumen of the catheter;

expanding the occlusion element to substantially occlude the renal blood vessel;

withdrawing the guide wire in a proximal direction to enable the control member to transform towards a preformed shape to contact an inner wall of the occlusion element adjacent to an inner wall of the renal blood vessel; and delivering neuromodulation energy via the neuromodulation element to inhibit neural communication along the renal nerve.

19. The method of claim 18, wherein the neuromodulation element is a direct heating element, wherein the direct heating element is a resistive heating element, and wherein delivering the neuromodulation energy includes delivering heat by applying an electrical current to the resistive heating element to deliver heat.

20. The method of claim 19, further comprising measuring a temperature of the resistive heating element during treatment and adjusting the electrical current applied to the resistive heating element to achieve a desired temperature.

21. The method of claim 18, wherein withdrawing the guide wire in the proximal direction enables the control member to transform towards the preformed shape to place the neuromodulation element in contact with the inner wall of the occlusion element.

* * * * *